(12) United States Patent
Noda et al.

(10) Patent No.: US 12,076,231 B2
(45) Date of Patent: Sep. 3, 2024

(54) INTRAOCULAR LENS INJECTOR

(71) Applicant: Hoya Corporation, Tokyo (JP)

(72) Inventors: Masahiro Noda, Toda (JP); Yoshitaka Watanabe, Tokyo (JP)

(73) Assignee: Hoya Corporation, Tokyo (JP)

( * ) Notice: Subject to any disclaimer, the term of this patent is extended or adjusted under 35 U.S.C. 154(b) by 597 days.

(21) Appl. No.: 17/055,253

(22) PCT Filed: Apr. 25, 2019

(86) PCT No.: PCT/JP2019/017743
§ 371 (c)(1),
(2) Date: Feb. 13, 2021

(87) PCT Pub. No.: WO2019/225292
PCT Pub. Date: Nov. 28, 2019

(65) Prior Publication Data
US 2021/0161653 A1    Jun. 3, 2021

(30) Foreign Application Priority Data

May 25, 2018    (JP) ................................. 2018-100534

(51) Int. Cl.
*A61F 2/16*    (2006.01)
(52) U.S. Cl.
CPC .................................. *A61F 2/167* (2013.01)
(58) Field of Classification Search
CPC ...... A61F 2/167; A61F 2/1662; A61F 2/1667; A61F 2/1672; A61F 9/00; A61F 9/0008; A61F 9/007; A61M 5/3137
See application file for complete search history.

(56) References Cited

U.S. PATENT DOCUMENTS 2,761,446 A    9/1956 Reed
3,212,685 A    10/1965 Swan
(Continued)

FOREIGN PATENT DOCUMENTS

CN    101073519 A    11/2007
CN    204601363 U    9/2015
(Continued)

OTHER PUBLICATIONS

U.S. Appl. No. 17/435,762, filed Sep. 2, 2021.
(Continued)

*Primary Examiner* — Sarah W Aleman
(74) *Attorney, Agent, or Firm* — Henricks Slavin LLP

(57) ABSTRACT

There is provided an intraocular lens injector capable of smoothly performing an operation when an intraocular lens is injected, the intraocular lens injector, including:
 a hollow body 5 having a lens setting portion 11 on which an intraocular lens 4 is set;
 a plunger 9 that moves through an inside of the hollow body 5 in an axial direction of the hollow body 5;
 a pushing member 10 that pushes out the intraocular lens 4 from the lens setting portion 11 by moving together with the plunger 9, through the inside of the hollow body 5, and toward front part of the axial direction of the hollow body 5;
 a first flange 14*a* protruded from an outer circumferential surface of the hollow body 5; and
 a second flange 14*b* arranged on a rear end side with respect to the first flange and protruded from the outer circumferential surface of the hollow body 5;
 wherein the hollow body 5 is configured so that a shape on the A direction side toward a center of gravity of the hollow body 5 in which the first flange 14*a* is arranged from a center O of the hollow body 5, and a shape on
(Continued)

the A' direction side which is the opposite direction to the A direction, are non-symmetrical, when viewed from the axial direction, and the second flange 14b is configured to protrude toward at least the A' direction, and the first flange 14a is configured not to protrude toward the A' direction, or configured so that a protruding distance of the first flange 14a toward the A' direction is smaller than a protruding distance Ha of the first flange toward the A direction and smaller than a protruding distance Hb of the second flange toward the A' direction.

14 Claims, 9 Drawing Sheets

(56) References Cited

U.S. PATENT DOCUMENTS

| | | |
|---|---|---|
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A | 3/1989 | Haber et al. |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,178,622 A | 1/1993 | Lehner, II |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A | 9/1999 | Bendek et al. |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,050,999 A | 4/2000 | Paraschac et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |

(56) References Cited

U.S. PATENT DOCUMENTS

| | | |
|---|---|---|
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,503,275 B1 | 1/2003 | Cumming |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,605,093 B1 | 8/2003 | Blake |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,749,631 B1 | 6/2004 | Pietrini et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,526 B2 | 7/2013 | Pynson |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 8,647,382 B2 | 2/2014 | Kudo et al. |
| 8,702,795 B2 | 4/2014 | Shoji et al. |
| 8,747,465 B2 | 6/2014 | Someya et al. |
| 8,968,328 B2 | 3/2015 | Ichinohe et al. |
| 9,114,006 B2 | 8/2015 | Inoue |
| 9,114,007 B2 | 8/2015 | Ichinohe et al. |
| 9,186,246 B2 | 11/2015 | Inoue |
| 9,220,593 B2 | 12/2015 | Ichinohe |
| 9,289,288 B2 | 3/2016 | Someya et al. |
| 9,314,373 B2 | 4/2016 | Kudo et al. |
| 9,326,847 B2 * | 5/2016 | Sanger ............... A61F 2/1672 |
| 9,364,320 B2 | 6/2016 | Ichinohe et al. |
| 9,554,894 B2 | 1/2017 | Inoue |
| 9,572,710 B1 | 2/2017 | Kudo et al. |
| 9,655,718 B2 | 5/2017 | Kudo |
| 9,687,340 B2 | 6/2017 | Anderson |
| 9,877,826 B2 | 1/2018 | Kudo et al. |
| 9,901,442 B2 | 2/2018 | Kudo et al. |
| 9,907,647 B2 | 3/2018 | Inoue |
| 9,980,811 B2 | 5/2018 | Kudo et al. |
| 10,039,668 B2 | 8/2018 | Kudo et al. |
| 10,231,826 B2 | 5/2019 | Hangya et al. |
| 10,383,723 B2 | 8/2019 | Kudo |
| 10,390,940 B2 | 8/2019 | Someya et al. |
| 10,405,971 B2 | 9/2019 | Someya et al. |
| 10,517,717 B2 | 12/2019 | Inoue |
| 10,799,339 B2 | 10/2020 | Kudo et al. |
| 10,849,738 B2 | 12/2020 | Kudo et al. |
| 11,033,382 B2 | 6/2021 | Watanabe et al. |
| 11,439,499 B2 | 9/2022 | Wensrich et al. |
| 11,938,019 B2 | 3/2024 | Someya et al. |
| 2001/0007942 A1 | 7/2001 | Kikuchi et al. |
| 2001/0020171 A1 | 9/2001 | Heyman |
| 2002/0103490 A1 | 8/2002 | Brady |
| 2002/0151904 A1 | 10/2002 | Feingold et al. |
| 2002/0165610 A1 | 11/2002 | Waldock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212408 A1 | 11/2003 | Kobayashi |
| 2003/0212409 A1 | 11/2003 | Kobayashi et al. |
| 2004/0039345 A1 | 2/2004 | Benz et al. |
| 2004/0111094 A1 | 6/2004 | Meyer |
| 2004/0116937 A1 | 6/2004 | Portney |
| 2004/0117012 A1 | 6/2004 | Vincent |
| 2004/0127911 A1 | 7/2004 | Figueroa |
| 2004/0147938 A1 | 7/2004 | Dusek et al. |
| 2004/0186428 A1 | 9/2004 | Ray |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0055011 A1 | 3/2005 | Enggaard |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek |
| 2006/0142781 A1 | 6/2006 | Pynson et al. |
| 2006/0167466 A1 | 7/2006 | Dusek |
| 2006/0173540 A1 | 8/2006 | Vincent |
| 2006/0200167 A1 | 9/2006 | Peterson et al. |
| 2006/0229633 A1 | 10/2006 | Shepherd |
| 2006/0235429 A1 | 10/2006 | Lee et al. |
| 2006/0293694 A1 | 12/2006 | Futamura |
| 2007/0000801 A1 | 1/2007 | Mauran et al. |
| 2007/0005135 A1 | 1/2007 | Makker et al. |
| 2007/0168026 A1 | 7/2007 | Nagasaka |
| 2007/0173860 A1 | 7/2007 | Iwasaki |
| 2007/0270945 A1 | 11/2007 | Kobayashi |
| 2008/0027460 A1 | 1/2008 | Kobayashi |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2009/0270876 A1 | 10/2009 | Hoffmann et al. |

(56) References Cited

U.S. PATENT DOCUMENTS

| | | |
|---|---|---|
| 2009/0292293 A1 | 11/2009 | Bogaert et al. |
| 2010/0082037 A1 | 4/2010 | Kobayashi et al. |
| 2010/0094309 A1 | 4/2010 | Boukhny et al. |
| 2010/0106160 A1 | 4/2010 | Tsai |
| 2010/0161049 A1 | 6/2010 | Inoue |
| 2010/0185206 A1 | 7/2010 | Ichinohe et al. |
| 2010/0217273 A1 | 8/2010 | Someya et al. |
| 2010/0286704 A1 | 11/2010 | Ichinohe et al. |
| 2010/0331808 A1 | 12/2010 | Py et al. |
| 2011/0046633 A1 | 2/2011 | Pankin et al. |
| 2011/0046635 A1 | 2/2011 | Pankin et al. |
| 2011/0082463 A1 | 4/2011 | Inoue |
| 2011/0098717 A1 | 4/2011 | Inoue |
| 2011/0144654 A1 | 6/2011 | Isaacs et al. |
| 2011/0172676 A1 | 7/2011 | Chen |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022548 A1 | 1/2012 | Zacharias |
| 2012/0022549 A1 | 1/2012 | Someya et al. |
| 2012/0071887 A1 | 3/2012 | Ichinohe et al. |
| 2012/0123438 A1 | 5/2012 | Horvath et al. |
| 2012/0221102 A1 | 8/2012 | Tanaka et al. |
| 2013/0006259 A1 | 1/2013 | Sanger |
| 2013/0018460 A1 | 1/2013 | Anderson |
| 2013/0085507 A1 | 4/2013 | Nagasaka |
| 2013/0226193 A1 | 8/2013 | Kudo et al. |
| 2013/0245635 A1 | 9/2013 | Inoue |
| 2013/0345713 A1 | 12/2013 | Cole et al. |
| 2014/0081284 A1 | 3/2014 | Ichinohe et al. |
| 2014/0107660 A1 | 4/2014 | Ichinohe et al. |
| 2014/0114323 A1 | 4/2014 | Kudo et al. |
| 2014/0135784 A1* | 5/2014 | Maroscheck ......... A61F 2/1678 606/107 |
| 2014/0180299 A1 | 6/2014 | Ichinohe et al. |
| 2014/0180300 A1 | 6/2014 | Ichinohe et al. |
| 2014/0194890 A1 | 7/2014 | Kudo et al. |
| 2014/0200588 A1* | 7/2014 | Anderson ............. A61F 2/1672 606/107 |
| 2014/0276901 A1 | 9/2014 | Auld |
| 2014/0296863 A1 | 10/2014 | Anderson et al. |
| 2015/0045805 A1* | 2/2015 | Kontur .................. A61F 2/1678 606/107 |
| 2015/0157500 A1 | 6/2015 | Midorikawa |
| 2015/0327992 A1 | 11/2015 | Wagner et al. |
| 2016/0000556 A1 | 1/2016 | Perera |
| 2016/0058554 A1 | 3/2016 | Anderson et al. |
| 2016/0113759 A1 | 4/2016 | Inoue |
| 2016/0151150 A1 | 6/2016 | Sato |
| 2016/0193038 A1 | 7/2016 | Kudo et al. |
| 2016/0256316 A1* | 9/2016 | Van Noy ............. A61F 9/00736 |
| 2016/0270907 A1 | 9/2016 | Attinger |
| 2016/0331587 A1 | 11/2016 | Yamada et al. |
| 2016/0346077 A1 | 12/2016 | Someya et al. |
| 2017/0079772 A1 | 3/2017 | Kudo |
| 2017/0119522 A1 | 5/2017 | Auld et al. |
| 2017/0151056 A1 | 6/2017 | Inoue |
| 2017/0202662 A1 | 7/2017 | Someya et al. |
| 2017/0252149 A1 | 9/2017 | Kudo et al. |
| 2017/0252150 A1 | 9/2017 | Kudo et al. |
| 2017/0258582 A1 | 9/2017 | Kudo et al. |
| 2017/0354493 A1 | 12/2017 | Andersen et al. |
| 2018/0014996 A1 | 1/2018 | Asbaghi |
| 2018/0200046 A1 | 7/2018 | Brown et al. |
| 2018/0250125 A1 | 9/2018 | Kudo et al. |
| 2018/0353287 A1 | 12/2018 | Kudo et al. |
| 2019/0151078 A1 | 5/2019 | Watanabe et al. |
| 2019/0192284 A1 | 6/2019 | Watanabe et al. |
| 2020/0113674 A1 | 4/2020 | Someya et al. |
| 2021/0145570 A1 | 5/2021 | Kudo |
| 2022/0151767 A1 | 5/2022 | Kudo |
| 2023/0033115 A1 | 2/2023 | Watanabe et al. |
| 2023/0225858 A1 | 7/2023 | Someya et al. |
| 2023/0301833 A1 | 9/2023 | Wu |
| 2023/0372083 A1 | 11/2023 | Kudo |

FOREIGN PATENT DOCUMENTS

| | | |
|---|---|---|
| DE | 3610925 | 10/1987 |
| DE | 4110278 | 10/1992 |
| DE | 19544119 A1 | 5/1997 |
| DE | 20219445 U1 | 3/2003 |
| EP | 0363213 | 4/1990 |
| EP | 0727966 | 9/2003 |
| EP | 1360947 A1 | 11/2003 |
| EP | 1502559 A1 | 7/2004 |
| EP | 1502559 A1 | 2/2005 |
| EP | 1790317 A2 | 5/2007 |
| EP | 1808150 A1 | 7/2007 |
| EP | 1832247 A1 | 9/2007 |
| EP | 1338254 | 12/2008 |
| EP | 2074961 A1 | 7/2009 |
| EP | 2255751 A1 | 12/2010 |
| EP | 2286763 A1 | 2/2011 |
| EP | 2286764 A1 | 2/2011 |
| EP | 2368526 A1 | 9/2011 |
| EP | 2574308 A2 | 4/2013 |
| EP | 2853236 A2 | 4/2015 |
| FR | 2749752 A | 12/1997 |
| JP | 63-197453 A | 8/1988 |
| JP | 4-212350 A | 8/1992 |
| JP | 5-103803 A | 4/1993 |
| JP | 5-103808 | 4/1993 |
| JP | 5-103809 | 4/1993 |
| JP | 08-019558 A | 1/1996 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2001-259033 | 9/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-527162 A | 9/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-041271 A | 2/2004 |
| JP | 2004-188194 A | 7/2004 |
| JP | 2004-344213 A | 12/2004 |
| JP | 2004-351196 A | 12/2004 |
| JP | 2006-014963 A | 1/2006 |
| JP | 2006-181269 A | 7/2006 |
| JP | 2006-297146 A | 11/2006 |
| JP | 2006-333924 A | 12/2006 |
| JP | 2006-333980 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-222309 A | 9/2007 |
| JP | 2007-244570 A | 9/2007 |
| JP | 2007-526091 A | 9/2007 |
| JP | 2007-307168 A1 | 11/2007 |
| JP | 2008-012016 A | 1/2008 |
| JP | 2008-521535 A | 6/2008 |
| JP | 2008-212689 A | 9/2008 |
| JP | 2008-237274 A | 10/2008 |
| JP | 2009-028223 A | 2/2009 |
| JP | 2009-028233 A | 2/2009 |
| JP | 2009-072221 A | 4/2009 |
| JP | 2011-019987 A | 2/2011 |
| JP | 2011-087976 A | 5/2011 |
| JP | 2011-160858 A | 8/2011 |
| JP | 2011-160859 A | 8/2011 |
| JP | 2013-144163 A | 7/2013 |

(56) References Cited

FOREIGN PATENT DOCUMENTS

| | | | |
|---|---|---|---|
| JP | 2014-050484 A | 3/2014 | |
| JP | 2014-079630 A | 5/2014 | |
| JP | 2016-137122 A | 8/2016 | |
| WO | WO9407436 A1 | 4/1994 | |
| WO | WO9513022 A1 | 5/1995 | |
| WO | WO9628122 A1 | 9/1996 | |
| WO | WO9715253 A1 | 5/1997 | |
| WO | WO9812969 A1 | 4/1998 | |
| WO | WO9937247 A1 | 7/1999 | |
| WO | WO9958086 A1 | 11/1999 | |
| WO | WO9959668 A1 | 11/1999 | |
| WO | WO0045746 A1 | 8/2000 | |
| WO | WO0062712 A1 | 10/2000 | |
| WO | WO2002071982 A1 | 9/2002 | |
| WO | WO2002096322 A1 | 12/2002 | |
| WO | WO2004/041323 A2 | 5/2004 | |
| WO | WO2004105649 A1 | 12/2004 | |
| WO | WO2005023154 A1 | 3/2005 | |
| WO | WO2005030097 A1 | 4/2005 | |
| WO | WO2005070341 A1 | 8/2005 | |
| WO | WO2005084588 A1 | 9/2005 | |
| WO | WO2006070628 A1 | 7/2006 | |
| WO | WO2006080191 A1 | 8/2006 | |
| WO | WO2006090531 A1 | 8/2006 | |
| WO | WO2007037223 A1 | 4/2007 | |
| WO | WO2007097221 A1 | 4/2007 | |
| WO | WO2007080869 A1 | 7/2007 | |
| WO | WO2008149794 A1 | 12/2008 | |
| WO | WO2008149795 A1 | 12/2008 | |
| WO | WO2009058929 A1 | 7/2009 | |
| WO | WO2009148091 A1 | 12/2009 | |
| WO | WO2010028873 A1 | 3/2010 | |
| WO | WO2010064970 A1 | 6/2010 | |
| WO | WO2011126144 A1 | 10/2011 | |
| WO | WO2011155636 A1 | 12/2011 | |
| WO | WO2012086797 A1 | 6/2012 | |
| WO | WO2012155887 A1 | 11/2012 | |
| WO | WO2015012312 A1 | 1/2015 | |
| WO | WO2016191764 A1 | 12/2016 | |
| WO | WO-2018003854 A1 * | 1/2018 | ............... A61F 2/16 |
| WO | WO-2019130028 A1 * | 7/2019 | ............. A61F 2/167 |

OTHER PUBLICATIONS

U.S. Appl. No. 16/313,184, filed Dec. 26, 2018, US 20190151078A1.
U.S. Appl. No. 17/055,253, filed Nov. 13, 2020.
U.S. Appl. No. 17/055,186, filed Nov. 13, 2020.
U.S. Appl. No. 17/801,364, filed Aug. 22, 2022.
Presentation given by James P. McCulley, titled "Benefits of Newest Generation Fully Preloaded Aspheric IOL Delivery System," on Sep. 16, 2008 at the "Aspheric IOLs" free paper session of the 2008 Congress of the European Society of Cataract and Refractive Surgery, in Berlin, Germany.
U.S. Appl. No. 16/550,144, filed Aug. 23, 2019, US 20200113674A1.
English Translation of PCT International Preliminary Examination Report dated Dec. 10, 2020 for PCT App. Ser. No. PCT/JP2019/017743.
PCT International Search Report dated Jun. 18, 2019 for PCT App. Ser. No. PCT/JP2019/017743.
U.S. Appl. No. 12/602,442, filed Dec. 15, 2009, U.S. Pat. No. 8,747,465.
U.S. Appl. No. 13/244,449, filed Sep. 24, 2011, U.S. Pat. No. 9,289,288.
U.S. Appl. No. 15/063,395, filed Mar. 7, 2016, U.S. Pat. No. 10,390,940.
U.S. Appl. No. 15/476,717, filed Mar. 31, 2017, U.S. Pat. No. 10,405,971.
U.S. Appl. No. 16/550,144, filed Aug. 23, 2019, U.S. Pat. No. 11,617,643.
U.S. Appl. No. 18/186,167, filed Mar. 18, 2023, US 20230225858A1.
U.S. Appl. No. 12/602,454, filed Dec. 15, 2009, U.S. Pat. No. 8,475,528.
U.S. Appl. No. 13/244,452, filed Sep. 24, 2011, U.S. Pat. No. 8,535,375.
U.S. Appl. No. 12/667,510, filed Dec. 31, 2009, U.S. Pat. No. 9,114,006.
U.S. Appl. No. 14/812,104, filed Jul. 29, 2015, U.S. Pat. No. 9,907,647.
U.S. Appl. No. 12/995,263, filed Dec. 15, 2010, U.S. Pat. No. 9,554,894.
U.S. Appl. No. 15/382,377, filed Dec. 16, 2016, U.S. Pat. No. 10,517,717.
U.S. Appl. No. 12/997,651, filed Dec. 13, 2010, U.S. Pat. No. 8,382,769.
U.S. Appl. No. 13/757,790, filed Feb. 2, 2012, U.S. Pat. No. 9,186,246.
U.S. Appl. No. 13/583,216, filed Apr. 6, 2011, U.S. Pat. No. 9,326,847.
U.S. Appl. No. 13/699,708, filed Jun. 8, 2011, U.S. Pat. No. 8,647,382.
U.S. Appl. No. 14/145,846, filed Dec. 31, 2013, U.S. Pat. No. 9,314,373.
U.S. Appl. No. 15/071,880, filed Mar. 16, 2016, U.S. Pat. No. 10,039,668.
U.S. Appl. No. 15/336,678, filed Oct. 27, 2016, U.S. Pat. No. 9,572,710.
U.S. Appl. No. 15/608,895, filed May 30, 2017, U.S. Pat. No. 9,980,811.
U.S. Appl. No. 13/059,401, filed Feb. 16, 2011, U.S. Pat. No. 8,702,795.
U.S. Appl. No. 13/061,143, filed Feb. 26, 2011, U.S. Pat. No. 8,470,032.
U.S. Appl. No. 13/143,322, filed Jul. 5, 2011, U.S. Pat. No. 8,603,103.
U.S. Appl. No. 14/099,989, filed Dec. 8, 2013, U.S. Pat. No. 9,655,718.
U.S. Appl. No. 15/600,679, filed May 19, 2017, U.S. Pat. No. 9,877,826.
U.S. Appl. No. 15/600,684, filed May 19, 2017, U.S. Pat. No. 9,901,442.
U.S. Appl. No. 11/814,508, filed Jul. 23, 2007, U.S. Pat. No. 8,545,512.
U.S. Appl. No. 14/033,888, filed Sep. 23, 2013, U.S. Pat. No. 9,220,593.
U.S. Appl. No. 11/816,676, filed Aug. 20, 2007, U.S. Pat. No. 8,523,877.
U.S. Appl. No. 13/966,209, filed Aug. 13, 2013, U.S. Pat. No. 9,364,320.
U.S. Appl. No. 12/095,172, filed May 28, 2008, U.S. Pat. No. 8,523,941.
U.S. Appl. No. 14/011,018, filed Aug. 27, 2013, U.S. Pat. No. 8,968,328.
U.S. Appl. No. 12/088,328, filed Mar. 27, 2008, U.S. Pat. No. 8,574,239.
U.S. Appl. No. 14/065,365, filed Oct. 28, 2013, U.S. Pat. No. 9,114,007.
U.S. Appl. No. 11/722,601, filed Apr. 10, 2008, U.S. Pat. No. 8,460,311.
U.S. Appl. No. 15/126,277, filed Sep. 14, 2016, U.S. Pat. No. 10,383,723.
U.S. Appl. No. 15/756,565, filed Feb. 28, 2018, U.S. Pat. No. 10,849,738.
U.S. Appl. No. 15/756,569, filed Feb. 28, 2018, U.S. Pat. No. 10,799,339.
U.S. Appl. No. 16/313,180, filed Dec. 26, 2018, US 20190192284A1.
U.S. Appl. No. 16/313,184, filed Dec. 26, 2018, U.S. Pat. No. 11,033,382.
U.S. Appl. No. 17/055,253, filed Nov. 13, 2020, US 20210161653A1.
U.S. Appl. No. 17/055,186, filed Nov. 13, 2020, US 20210145570A1.
U.S. Appl. No. 17/435,762, filed Sep. 2, 2021, US 20220151767A1.
U.S. Appl. No. 17/801,364, filed Aug. 22, 2022, US 20230033115A1.
U.S. Appl. No. 18/044,235, filed Mar. 7, 2023, US 20230372083A1.

* cited by examiner

INTRAOCULAR LENS INJECTOR

TECHNICAL FIELD

The present invention relates to an intraocular lens injector.

DESCRIPTION OF RELATED ART

Cataract surgery involves the removal of a cloudy crystalline lens by ultrasonic emulsification followed by implantation of an intraocular lens into an eye. Currently, an intraocular lens made of a soft material such as silicone elastomer is injected into an eye using an intraocular lens injector.

This kind of intraocular lens injector may have various shapes. For example, the intraocular lens injector described in Patent Document 1 has a plurality of handles 24 (flanges) that serve as members on which the operator places his/her fingers when injecting the intraocular lens 1, as illustrated in FIG. 4 of Patent Document 1.

PRIOR ART DOCUMENT

Patent Document

[Patent Document 1] Japanese Unexamined Patent Publication No. 2007-185255

SUMMARY OF THE INVENTION

Problem to be Solved by the Invention

The operation of the intraocular lens injector is very delicate. Therefore, it is an urgent problem to improve the workability of the operator. In particular, a smooth operation of the plunger at the time of injecting an intraocular lens contributes to a significant improvement in workability.

It is a technical problem of the present invention to provide an intraocular lens injector capable of smoothly performing an operation at the time of injecting an intraocular lens.

Means for Solving the Problem

The present inventors observed the condition of the operator's hand at the time of injecting the intraocular lens. In an example described in Patent Document 1, the arrangement of the flanges is vertically symmetrical, as illustrated in FIG. 4(b). With this arrangement, the operator does not feel much load on his/her fingers when he/she starts to push the plunger with his/her thumb, regardless of whether he/she puts his/her index finger and middle finger on the upper side and the lower side of the front flange, respectively, or he/she puts his/her index finger and middle finger on the upper side and the lower side of the rear flange, respectively. On the other hand, in the case of using the rear flange, the distance between the flange and the rear end portion of the plunger (the portion pressed by the thumb) is shortened when the plunger is finished being pressed, and the operator feels a large load on his/her fingers. A large load can be a factor which destabilizes an operation. When the front flange is used, the distance between the flange and the rear end of the plunger can be secured to some extent, but it is better to reduce the load on the operator, if possible.

Focusing on this point, the present inventors have devised a configuration in which a plurality of flanges is provided and the shape of the front flange is to be vertically non-symmetrical.

The configurations obtained based on the above findings are as follows.

A first aspect of the invention provides
an intraocular lens injector, including:
  a hollow body having a lens setting portion on which an intraocular lens is set;
  a plunger that moves through an inside of the hollow body in an axial direction of the hollow body;
  a pushing member that pushes out the intraocular lens from the lens setting portion by moving together with the plunger, through the inside of the hollow body, and toward front part of the axial direction of the hollow body;
  a first flange protruded from an outer circumferential surface of the hollow body; and
  a second flange arranged on a rear end side with respect to the first flange and protruded from the outer circumferential surface of the hollow body,
wherein the hollow body is configured so that a shape of the first flange on the A direction side toward a center of gravity of the hollow body in which the first flange is arranged from a center of the hollow body, and a shape of the first flange on the A' direction side which is the opposite direction to the A direction, are non-symmetrical, when viewed from the axial direction, and
the second flange is configured to protrude toward at least the A' direction, when the hollow body is viewed from the axial direction, and
the first flange is configured not to protrude toward the A' direction, or configured so that a protruding distance of the first flange toward the A' direction is smaller than a protruding distance of the first flange toward the A direction and smaller than a protruding distance of the second flange toward the A' direction.

A second aspect of the present invention is the invention according to the first aspect, wherein the first flange on the A direction side and the second flange on the A' direction side, are configured so that a protruding distance thereof is 10 mm or more.

A third aspect of the present invention is the invention according to the first or second aspect, wherein the lens setting portion is arranged on a tip end side with respect to the first flange, and the lens setting portion is arranged in the A direction when viewing the hollow body from the axial direction.

A fourth aspect of the present invention is the invention according to the first aspect,
  wherein the first flange on the A direction side and the second flange on the A' direction side, are configured so that a vertically protruding distance thereof in the axial direction of the hollow body is 10 mm or more,
  the lens setting portion is arranged on a tip end side with respect to the first flange, and
  the lens setting portion is arranged in the A direction when viewing the hollow body from the axial direction.

A fifth aspect of the present invention is the invention according to any one of the first to fourth aspects, wherein at least one of the first flange and the second flange has a configuration movable in the axial direction of the hollow body.

A sixth aspect of the present invention is the invention according to the fifth aspect, wherein indexes corresponding to at least one of the first
flange and the second flange are provided to the hollow
body, and at least one of the displayed indexes is varied
according to a movement of at least one of the first
flange and the second flange.

The protruding distances of the first flange on the A
direction side and the second flange on the A' direction side
are preferably 15 mm or more, and a preferable example of
the upper limit is 20 mm.

The separation distance between the first flange and the
second flange in the axial direction of the hollow body is
preferably 10 to 60 mm, and more preferably 10 to 35 mm.

Moreover, it is preferable that the second flange is provided as a distinct body separated from the first flange.

Furthermore, as for arrangement in the axial direction, the
first flange is preferably arranged closer to the second flange
compared to the midpoint of the distance between the nozzle
provided at the front tip end of the hollow body and the
second flange.

The protruding distances of the first flange and the second
flange may be the same or different from each other. When
they are different, it is preferable that the protruding distance
of the first flange is 50% or more (preferably 60% or more,
more preferably 60 to 140%, and still more preferably 80 to
120%) based on the protruding distance of the second flange.

Another aspect of the present invention is as follows. In
addition, the aspects and preferable examples of this
embodiment may be applied to each of other aspects
described below.

An intraocular lens injector, including:
a hollow body having a lens setting portion on which an
intraocular lens is set;
a plunger that moves through an inside of the hollow body
in an axial direction of the hollow body; and
a pushing member that pushes out the intraocular lens
from the lens setting portion by moving together with
the plunger, through the inside of the hollow body, and
in the axial direction of the hollow body; and
a flange that is provided in the hollow body and can move
in an axial direction of the hollow body.

The flange in the above aspect may be the only flange in
the intraocular lens injector. That is, it may be the only
flange before and after the movement of the flange.

Still another aspect of the present invention is as follows.
An adaptor for intraocular lens injector, including:
a hollow body having a lens setting portion on which an
intraocular lens is set;
a plunger that moves through an inside of the hollow body
in an axial direction of the hollow body;
a pushing member that pushes out the intraocular lens
from the lens setting portion by moving together with
the plunger, through the inside of the hollow body, and
in the axial direction of the hollow body; and
a second flange protruded from an outer circumferential
surface of the hollow body;
wherein the adaptor includes a first flange,
the hollow body is configured so that a shape of the first
flange on the A direction side toward a center of gravity
of the hollow body in which the first flange is arranged
from a center of the hollow body, and a shape of the
first flange on the A' direction side which is the opposite
direction to the A direction, are non-symmetrical, when
viewed from the axial direction after the adaptor is
attached to the intraocular lens injector;
the second flange is configured to protrude toward at least
the A' direction, when the hollow body is viewed from
the axial direction after the adaptor is attached to the
intraocular lens injector; and
the first flange is configured not to protrude toward the A'
direction, or configured so that a protruding distance of
the first flange toward the A' direction is smaller than a
protruding distance of the first flange toward the A
direction and smaller than a protruding distance of the
second flange toward the A' direction. The adapter in
the above-described aspect may further include an
adapter body (suitably semi-cylindrical) and an
engagement portion (e.g., an opening) that engages
with the flange.

Still another aspect of the present invention is as follows.
An adaptor for intraocular lens injector, including:
a hollow body having a lens setting portion on which an
intraocular lens is set;
a plunger that moves through an inside of the hollow body
in an axial direction of the hollow body; and
a pushing member that pushes out the intraocular lens
from the lens setting portion by moving together with
the plunger, through the inside of the hollow body, and
in the axial direction of the hollow body;
wherein the adaptor includes a first flange and a second
flange,
the hollow body is configured so that a shape of the first
flange on the A direction side toward a center of gravity
of the hollow body in which the first flange is arranged
from a center of the hollow body, and a shape of the
first flange on the A' direction side which is the opposite
direction to the A direction, are non-symmetrical, when
viewed from the axial direction after the adaptor is
attached to the intraocular lens injector;
the second flange is configured to protrude toward at least
the A' direction, when the hollow body is viewed from
the axial direction after the adaptor is attached to the
intraocular lens injector; and
the first flange is configured not to protrude toward the A'
direction, or configured so that a protruding distance of
the first flange toward the A' direction is smaller than a
protruding distance of the first flange toward the A
direction and smaller than a protruding distance of the
second flange toward the A' direction.

SUMMARY OF THE INVENTION

The present invention provides an intraocular lens injector
capable of smoothly performing an operation at the time of
injecting an intraocular lens.

BRIEF DESCRIPTION OF THE DRAWING

FIG. 9(a) illustrates the configuration before the movement of the flange, and FIG. 9(b) illustrates the configuration after movement of the flange.

DETAILED DESCRIPTION OF THE INVENTION

Embodiments of the present invention will be described hereafter, with reference to the drawings. In the present specification, "to" refers to a predetermined value or more and a predetermined value or less.

In this embodiment, in describing a relative positional relationship and a direction of movement and the like of each part of the intraocular lens injector, one of the X axis directions is defined as X1 direction, the other direction is defined as X2 direction, and one of the Y axis directions is defined as Y1 direction, the other direction is defined as Y2 direction, and one of the Z axis directions is defined as Z1 direction and the other direction is defined as Z2 direction, and X1 direction is defined as a tip end side (frontward), X2 direction is defined as a rear end side (rearward), Y1 direction is defined as a left side (leftward), and Y2 direction is defined as a right side (rightward), Z1 direction is defined as an upper side (upward), and Z2 direction is defined as a downside (downward). Among them, the X1 direction and X2 direction correspond to a length direction of the intraocular lens injector 1, and the Y1 direction and Y2 direction correspond to a width direction of the intraocular lens injector, and the Z1 direction and Z2 direction correspond to a height direction of the intraocular lens injector 1.

The main feature portion in this embodiment is the part relating to the flange. Therefore, the intraocular lens injector is depicted as a configuration simplified except for the part relating to the flange.

Of course, except for the part relating to the flange, the known configuration of the intraocular lens injector may be adopted. For example, the configuration of WO2018/003854 by the present applicant may be adopted. Unless otherwise described below, a known configuration of an intraocular lens (for example, a configuration of WO 2018/003854) may be adopted, as if fully set forth herein.

Figure 1:
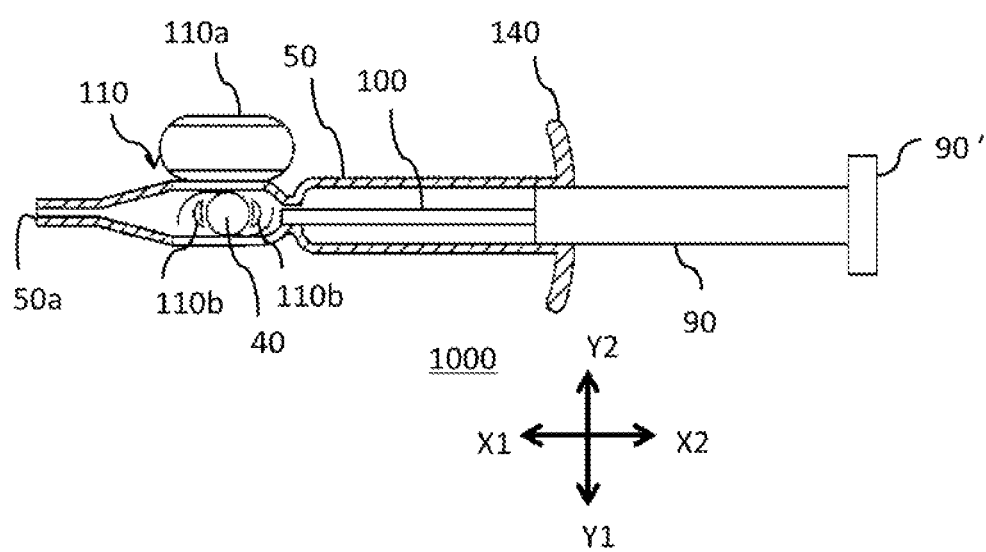
FIG. 1 is a schematic plan view of a conventional
intraocular lens injector.

FIG. 1 is a schematic plan view of the conventional intraocular lens injector 1000.

Figure 2:
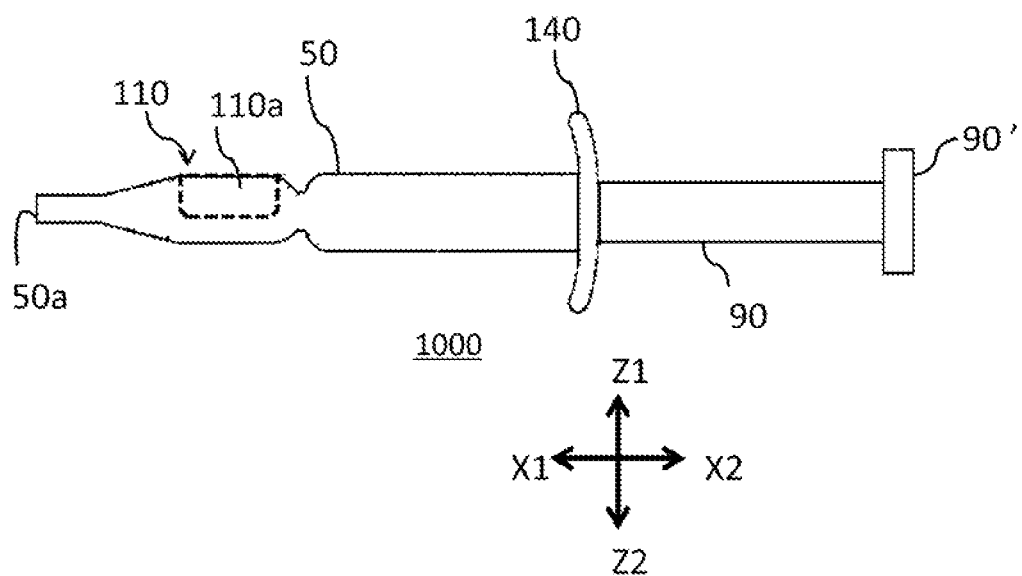
FIG. 2 is a schematic side view of a conventional
intraocular lens injector when viewed from the left side (Y1
direction).

FIG. 2 is a schematic side view of the conventional intraocular lens injector 1000 when viewed from the left side (Y1 direction).

Figure 3:
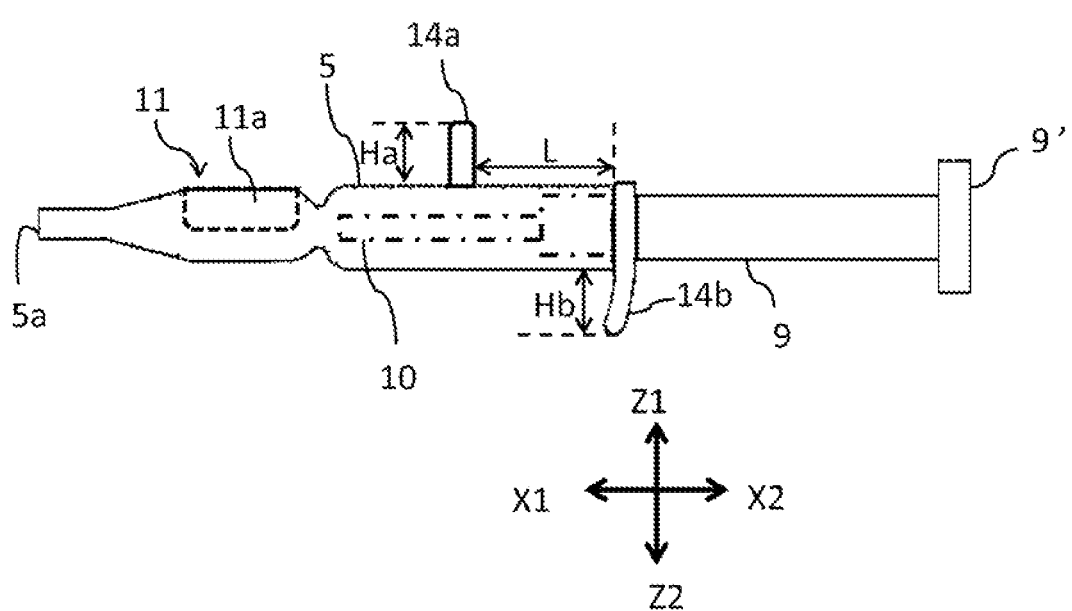
FIG. 3 is a schematic side view of an intraocular lens
injector of this embodiment when viewed from the left side
(Y1 direction).

This embodiment is illustrated in FIG. 3 based on the simplified configuration.

FIG. 3 is a schematic side view of the intraocular lens injector 1 of this embodiment when viewed from the left side (Y1 direction). A part of the plunger 9 and the pushing member 10 inside the intraocular lens injector 1 are indicated by a dash-dot-dash line.

Note that, in the conventional configuration of FIG. 1 and FIG. 2, a feature is indicated by a numeral of the corresponding feature of this embodiment of FIG. 3 with "zero" added after the last digit thereof.

An intraocular lens injector 1 of this embodiment includes:
a hollow body 5 having a lens setting portion 11 on which an intraocular lens 4 is set;
plunger 9 that moves through an inside of the hollow body 5 in an axial direction of the hollow body 5;
pushing member 10 that pushes out the intraocular lens 4 from the lens setting portion 11 by moving together with the plunger 9, through the inside of the hollow body 5, and in the axial direction of the hollow body 5;
first flange 14a protruded from an outer circumferential surface of the hollow body 5; and
second flange 14b arranged on a rear end side with respect to the first flange 14a and protruded from the outer circumferential surface of the hollow body 5.

The hollow body 5 is a main body of the intraocular lens injector 1. A lens setting portion 11 is provided at the front part side of the hollow body 5. The intraocular lens 4 is set on the lens setting portion 11.

The conventional configuration may be adopted for the configuration in the lens setting portion 11 of this embodiment. For example, in the conventional intraocular lens injector 1000, the intraocular lens 40 is held by the stopper 110b when the lid 110a of the lens setting portion 110 is opened, as illustrated in FIG. 1. At the time of injecting the intraocular lens 40, the stopper 110b is removed.

The lens setting portion 11 of this embodiment does not have to be provided with the openable/closable lid 11a. The intraocular lens 4 may already be set on the lens setting portion 11 at the shipping stage of the intraocular lens injector 1.

As the rear end 9' of the plunger 9 is pushed, the plunger 9 moves inside the hollow body 5 in the axial direction of the hollow body 5 to push the intraocular lens 4 from the tip end 5a (opening of the nozzle) of the hollow body 5. The plunger 9 is disposed coaxially with the hollow body 5. The plunger 9 is provided movably in the axial direction of the hollow body 5. The rear end 9' may have a shape that curves toward the rear end side to make it easier to receive the thumb of the operator (e. g., reference numeral 9' in FIGS. 4 and 5).

The pushing member 10 pushes the intraocular lens 4 set on the lens setting portion 11 forward, so that the intraocular lens 4 is released from the tip end 5a (opening of the nozzle) of the hollow body 5. Pushing member 10 is formed in an elongated rod shape. The pushing member 10 is coupled to the tip end part of the plunger 9 and moves integrally with the plunger 9 in the axial direction of the hollow body 5. The pushing member 10 may be integrally molded with the plunger 9.

One of the main characteristics of the first flange 14a is that the shape on the A direction side (Z1 direction side in this embodiment) and the shape on the A' direction side which is an opposite direction to the A direction (Z2 direction side in this embodiment) are non-symmetrical, when the hollow body 5 is viewed from the axial direction. It is one of the major differences from FIG. 2.

In view of the foregoing, one of the major characteristics is that the second flange 14b is configured to protrude toward at least the A' direction (toward Z2 direction), when the hollow body 5 is viewed from the axial direction.

Figure 7:
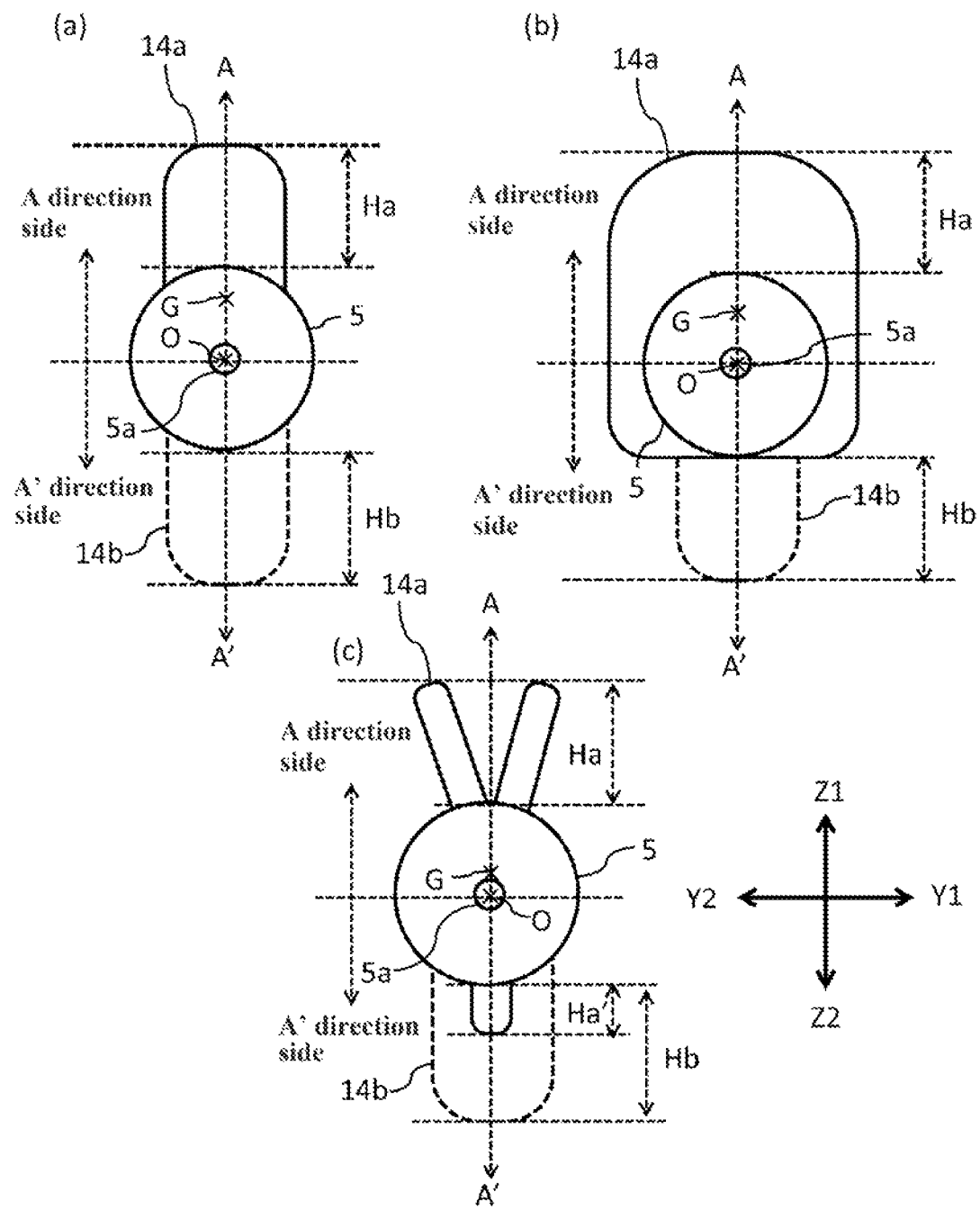
FIG. 7(a) is a schematic front view of the intraocular lens injector of this embodiment when viewed from the axial direction of the hollow body (X1 direction).
FIG. 7(b) and FIG. 7(c) are schematic front views of the intraocular lens injector of this embodiment when viewed from the axial direction of the hollow body (X1 direction), in which the first flange is deformed.

Moreover, one of the major characteristics is that the first flange 14a is configured not to protrude toward the A' direction (toward Z2 direction) (see, for example, FIG. 7(a), this embodiment adopts mainly this example), or configured so that a protruding distance Ha' of the first flange 14a toward the A' direction (toward Z2 direction) is smaller than a protruding distance Ha of the first flange 14a toward the A direction (toward Z1 direction) and smaller than a protruding distance Hb of the second flange 14b toward the A' direction (toward Z2 direction), as illustrated in FIG. 7(c) below.

"A direction" refers to the protruding direction of the first flange 14a. For example, in FIGS. 7 and 8 below, the Z1 direction corresponds to the A direction. More specifically, "A direction" refers to the direction from a center O of the hollow body 5 toward a center of gravity G of the hollow body 5 in which the first flange 14a is arranged, when viewing the hollow body 5 from the axial direction. The center of gravity G refers to a center of gravity in a configuration including the hollow body 5 and the first flange 14a when viewing the hollow body 5 from the axial direction. The center O usually coincides with the center of gravity of the cross section of the hollow body 5 before the first flange 14a is provided.

The "protruding distance" refers to a value obtained by subtracting the radius (half width) on the outer circumference side of the hollow body 5 from the distance between the first flange 14a or second flange 14b and the perpendicular line with respect to the A-A' direction, the perpendicular line passing through the center O of the hollow body 5, when viewing the hollow body 5 from the axial direction. The value being zero or less (for example, the A' direction side of the first flange 14a in FIG. 7(b)) means that there is no protrusion.

The A-A' direction (Z1-Z2 direction) means the two opposite directions on a straight line passing through an origin which is the center of the hollow body 5 on the YZ plane perpendicular to the axis of the hollow body 5, that is, the X axis.

The shape on the A direction side (Z1 direction side) refers to a shape in the area on the A direction side (upper side) with respect to the perpendicular line (Y1-Y2 direction) which passes through the center O of the hollow body 5 and is perpendicular to the A-A' direction (Z1-Z2 direction).

Similarly, the shape on the A' direction side (Z2 direction side) refers to a shape in the area on the A' direction side (lower side) with respect to the perpendicular line (Y1-Y2 direction) which passes through the center O of the hollow body 5 and is perpendicular to the A-A' direction (Z1-Z2 direction).

The first flange 14a is configured so as not to protrude toward the A' direction side (Z2 direction side), or so that the protruding distance of the first flange 14a on the A' direction side (Z2 direction side) is reduced as described above. Therefore, the first flange 14a has a non-symmetrical shape with respect to the perpendicular line (Y1-Y2 direction) which passes through the center O of the hollow body 5 and is perpendicular to the A-A' direction (Z1-Z2 direction).

The arrangement relationship and the magnitude relationship between the first flange 14a and the second flange 14b produce the following effects.

Figure 4:
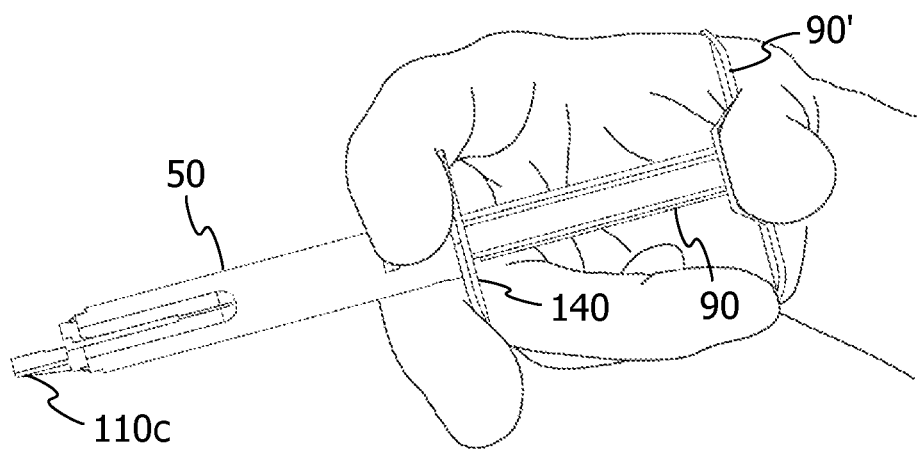
FIG. 4 is a schematic side view of a usage aspect of the
conventional intraocular lens injector.
Figure 4:
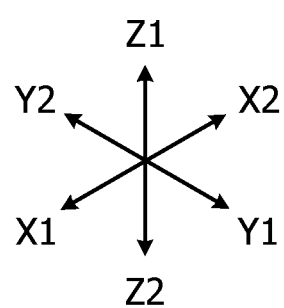

FIG. 4 is a schematic side view of a usage aspect of the conventional intraocular lens injector 1000.

Figure 5:
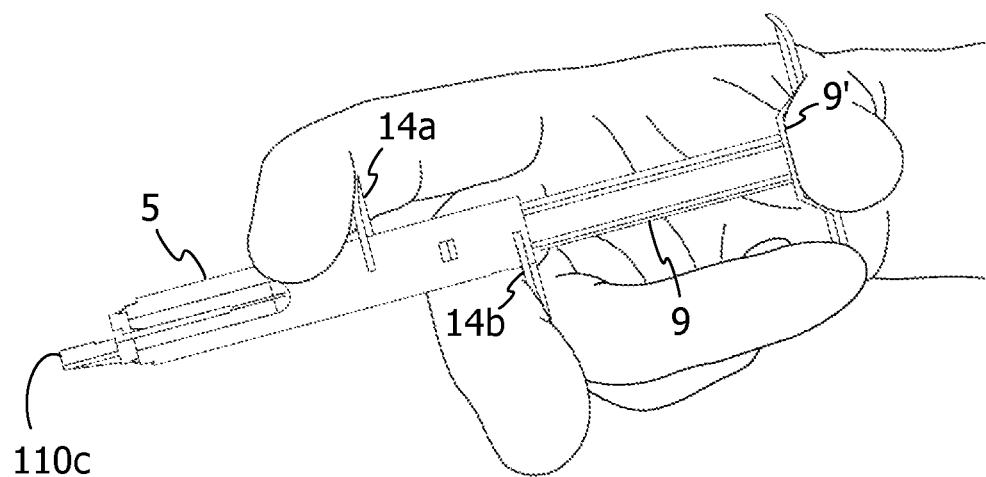
FIG. 5 is a schematic side view of a usage aspect of the
intraocular lens injector of this embodiment.
Figure 5:
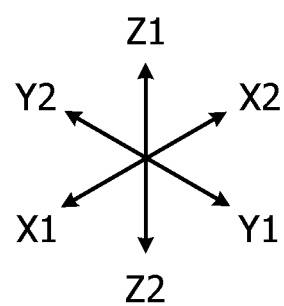

FIG. 5 is a schematic side view of a usage aspect of the intraocular lens injector 1 of this embodiment.

In the case where an operator uses the conventional intraocular lens injector 1000, as illustrated in FIG. 4, the distance between the flange 140 and the rear end portion 90' of the plunger 90 (the portion pressed by the thumb) is shortened when the plunger 90 is finished being pressed, and the operator feels a large load on his/her fingers.

On the other hand, in the case where an operator uses the intraocular lens injector 1 of this embodiment, as for the natural position of the operator's finger, his/her thumb presses against the plunger 9 while hooking his/her index finger on the first flange 14a protruding toward the A direction (Z1 direction) and his/her middle finger on the second flange 14b protruding toward the A' direction (Z2 direction) which is opposed to the A direction (Z1 direction), as illustrated in FIG. 5. At that time, the distance between the index finger and the thumb can be secured to be wider than before. This means that even when the plunger 9 is finished being pushed, the distance between the first flange 14a (index finger) and the rear end 9' of the plunger 9 (thumb) can be secured. The distance between the index finger on the first flange 14a and the plunger 9 is set to be larger than the distance between the middle finger on the second flange 14b and the plunger 9. This makes it easier for the operator to put his/her strength exclusively on his/her index finger, and thus the load on the operator can be reduced.

Figure 6:
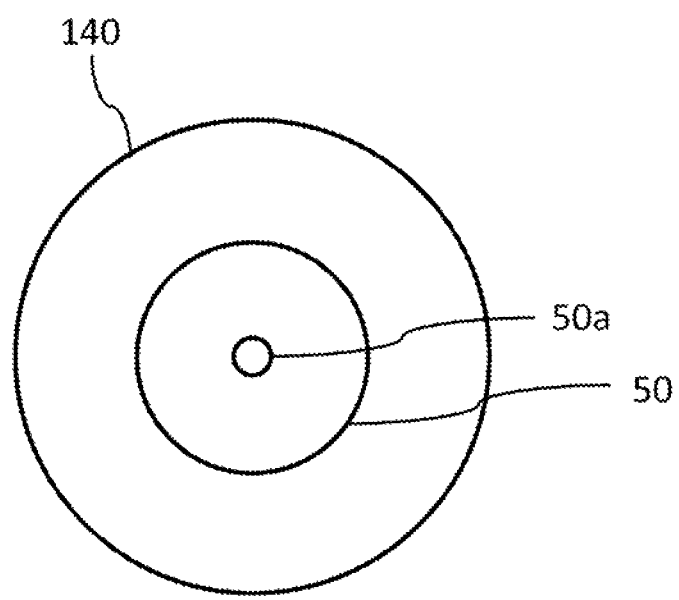
FIG. 6 is a schematic front view of the conventional
intraocular lens injector when viewed from the axial direction of the hollow body (X1 direction).
Figure 6:
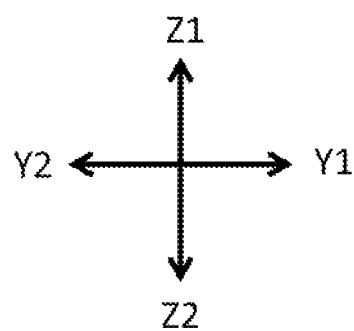

FIG. 6 is a schematic front view of the conventional intraocular lens injector 1000 when viewed from the axial direction of the hollow body 5 (X1 direction).

FIG. 7(a) is a schematic front view of the intraocular lens injector 1 of this embodiment when viewed from the axial direction of the hollow body 5 (X1 direction). FIG. 7(b) and FIG. 7(c) are schematic front views of the intraocular lens injector 1 of this embodiment when viewed from the axial direction of the hollow body 5 (X1 direction), in which the first flange 14a is deformed.

As illustrated in FIG. 6, as for the arrangement, the conventional flange 140 is provided protruding in an annular shape at the rear end of the hollow body 50. When the intraocular lens injector 1000 is viewed from the X1 direction, the flange 140 has a vertically symmetrical structure.

In contrast, the first flange 14a of this embodiment has a non-symmetrical structure (a structure in which the first flange 14a exists only on the upper side). Since the first flange 14a exists only on the upper side, the middle finger on the lower second flange 14b does not interfere with the first flange 14a. It greatly improves the operability of the operator.

Incidentally, the structure of the first flange 14a of this embodiment is, in other words, a structure that "is protruded from the outer circumferential surface of the hollow body 5 in the A direction of two directions, the A direction and the A' direction, that are opposite to each other". As illustrated in FIG. 7(a), this structure includes a structure that does not protrude in the right-left direction but only in the upward direction when the intraocular lens injector 1 is viewed from the axial direction of the hollow body 5 (the second flange 14b is indicated by dashed line). Also contemplated is the structure that protrudes in the right-left direction in addition to the upward direction, as illustrated in FIG. 7(b), when the intraocular lens injector 1 is viewed from the axial direction of the hollow body 5. Also contemplated is the structure having two or more protrusions as illustrated in FIG. 7(c).

In the first flange 14a which also protrudes toward the A' direction as illustrated in FIG. 7(c), when the protruding distance Ha' is smaller than the protruding distance Ha of the first flange 14a toward the A direction and smaller than the protruding distance Hb of the second flange 14b toward the A' direction, the middle finger on the lower second flange 14b does not interfere with the first flange 14a compared to those described in Patent Document 1.

In this case, the specific protruding distance Ha' of the first flange 14a toward the A' direction may be such that the middle finger does not interfere when the operator puts his/her middle finger on the second flange 14b. The distance may be, for example, less than 5 mm.

A second flange 14b protruding toward at least the A' direction (Z2 direction) is provided behind the first flange 14a. This is a major difference from the flange 140 of the conventional intraocular lens injector 1000.

In view of the foregoing, the intraocular lens injector 1 with the above configuration reduces the load on the operator's fingers, stabilizes the operation, and smoothly performs an operation at the time of injecting an intraocular lens 4.

The second flange 14b of this embodiment is provided as a distinct body, separated from the first flange 14a. The second flange 14b may protrude not only toward the A' direction (Z2 direction) but also toward the A direction (Z1 direction), or, like a conventional one, it may have a circular shape when viewed in the axial direction. In other words, the second flange 14b may have a conventional vertically symmetrical structure. In the following FIG. 8, the above description is reflected in a known intraocular lens injector 1.

Figure 8:
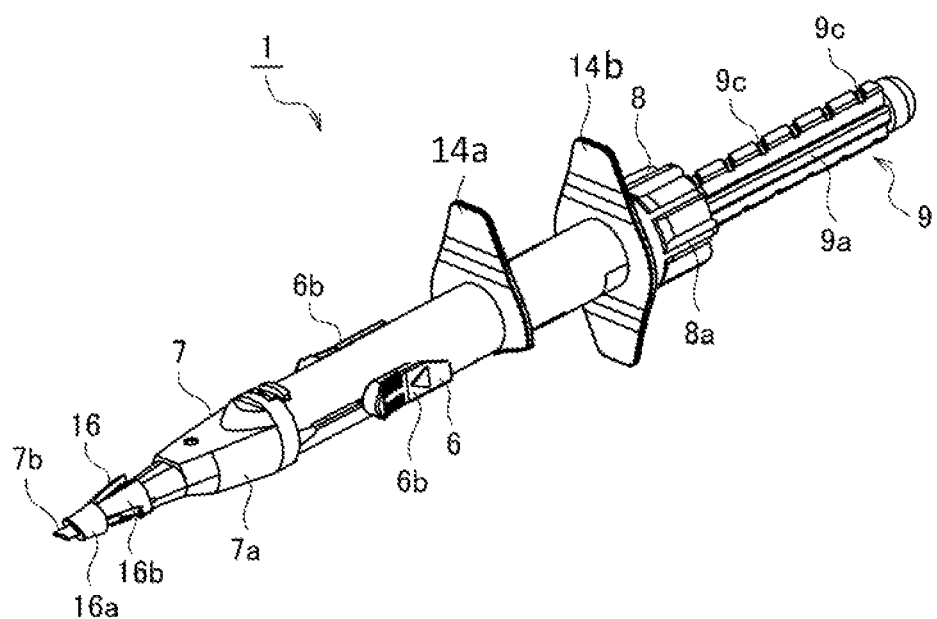
FIG. 8 is a schematic perspective view of this embodiment applied to the intraocular lens injector described in WO 2018/003854.

FIG. 8 is a schematic perspective view of this embodiment applied to the intraocular lens injector 1000 described in WO 2018/003854.

In FIG. 8, the same numeral as that in the present specification indicates one having the same configuration. The numerals described herein are as described in WO2018/003854.

The separation distance L between the first flange 14a and the second flange 14b in the axial direction of the hollow body 5 may be 10 to 60 mm, and is preferably 10 to 35 mm. With the distance being 10 mm or more, even when the plunger 9 is finished being pushed, the distance between the first flange 14a (index finger) and the rear end 9' of the plunger 9 (thumb) can be sufficiently secured. With the distance being 35 mm or less, the distance between the operator's index finger and thumb can be extended without difficulty.

Furthermore, as for arrangement in the X1-X2 direction, the first flange 14a is preferably arranged closer to the second flange compared to the midpoint of the distance between the tip end 5a of the hollow body 5 and the second flange 14b.

The separation distance L may be the distance in the X1-X2 direction when the operator puts his/her index finger on the first flange 14a and middle finger on the second flange 14b. By way of example of the definition of the separation distance L, it may be a distance between the protruding portion of the first flange 14a and the protruding portion of the second flange 14b on the outer circumference of the hollow body 5 in the axial direction of the hollow body 5, or may be the shortest distance between the first flange 14a and the second flange 14b.

The protruding distances Ha and Hb of the first flange 14a (toward the A direction (toward the Z1 direction)) and the second flange 14b (toward the A' direction (toward the Z2 direction)) in the vertical direction to the axial direction of the hollow body 5 are preferably 10 mm or more. With the distance being 10 mm or more, the operator's fingers are sufficiently caught on the first flange 14a and the second flange 14b, so that the operability can be further improved. The distance is preferably 15 mm or more. There is no particular limitation on the upper limit of the protruding distances Ha and Hb. However, with the protruding distances Ha and Hb being 20 mm or less, the operative field during the surgical procedure can be secured to be sufficiently wide, and the operator can visually recognize how the intraocular lens 4 is injected into the eye without hindrance.

In the case where the protruding distances Ha and Hb of the first flange 14a (toward the A direction (toward the Z1 direction)) and the second flange 14b (toward the A' direction (toward the Z2 direction)) in the vertical direction to the axial direction of the hollow body 5 are 10 mm or more, there is no limitation on the direction and shape of the protrusion, as long as it is protruded from the outer circumferential surface of the hollow body 5 when viewing the hollow body 5 from the axial direction. For example, even when protruding toward the front or toward the rear, the first flange 14a appears to protrude in the A direction (Z1 direction) when viewing the hollow body 5 from the axial direction. The above-described protruding distances Ha and Hb are determined based on this appearance.

The protruding distances Ha and Hb of the first flange 14a (toward the A direction (toward the Z1 direction)) and the second flange 14b (toward the A' direction (toward the Z2 direction)) may be the same or different from each other. When they are different, it is preferable that the protruding distance Ha of the first flange 14a (toward the A direction (toward the Z1 direction)) is 50% or more (preferably 60% or more, more preferably 60 to 140%, and still more preferably 80 to 120%) based on the protruding distance Hb of the second flange 14b (toward the A' direction (toward the Z2 direction)).

The lens setting portion 11 is arranged on the tip end side with respect to the first flange 14a, and then the lens setting portion 11 is preferably arranged in the A direction (Z1 direction), when the hollow body 5 is viewed from the axial direction. More specifically, when the hollow body 5 is cross-sectionally viewed with respect to the YZ plane, the lid 11a of the lens setting portion 11 (or inlet for hyaluronic acid, a window for monitoring the intraocular lens 4, etc.) is preferably provided on the outer circumference of the hollow body 5 in the A direction (Z1 direction). Namely, it is preferable that the direction in which the lens setting portion 11 is arranged, that is, the direction in which the optical surface of the intraocular lens 4 faces upward is same as the direction in which the first flange 14a protrudes.

When the operator grasps the intraocular lens injector 1 of this configuration, the lens setting portion 11 is naturally in the upper position as illustrated in FIG. 5. When the operator injects the intraocular lens 4 into the patient's eye, the operator naturally puts his/her index finger on the first flange 14a and middle finger on the second flange 14b. Therefore, the operator can observe the intraocular lens 4 being pushed out of the lens setting portion 11 while taking a natural posture.

It is preferable that at least one of the first flange 14a and the second flange 14b has a configuration movable in the axial direction of the hollow body 5. A shorter distance between the tip end 5a of the hollow body 5, that is, the opening of the nozzle through which the intraocular lens 4 is pushed out, and the first flange 14a may allow some operators to more smoothly perform an operation at the time of injecting the intraocular lens 4. With the above configuration, it is possible to meet this type of request tailored to a particular operator.

Alternatively, both of the first flange 14a and the second flange 14b may have a configuration movable in the axial direction of the hollow body 5. A "configuration movable" means a configuration that can be movable in the axial direction, and fixed in an arbitrary position after movement.

With this configuration, even when the plunger 9 is finished being pushed while the distance between the first flange 14a and the second flange 14b is kept constant, the distance between the first flange 14a (index finger) and the rear end 9' of the plunger 9 (thumb) can be secured. Then, the distance between the tip end 5a of the hollow body 5 and the first flange 14a can be shortened, as requested by the operator. As a result, an operation at the time of injecting an intraocular lens 4 can be performed very smoothly.

Alternatively, only the second flange 14b may have a configuration movable in the axial direction of the hollow body 5. With this configuration, the distance between the first flange 14a and the second flange 14b can be varied, tailored to the operator.

As the specific configuration movable in the axial direction of the hollow body 5, for example, a configuration may be adopted, in which at least one of the first flange 14a and the second flange 14b may be rotated about the axial direction of the hollow body 5 as a central axis, so as to be moved forward and backward. Alternatively, at least one of the first flange 14a and the second flange 14b may be pushed in the axial direction of the hollow body 5 so as to be moved. A notch or the like for locking at least one of the first flange 14a and the second flange 14b may be provided at a predetermined position in the axial direction of the hollow body 5.

It is preferable that the hollow body 5 is provided with index N according to the arrangement of at least one of the first flange 14a and the second flange 14b. It is preferable that the displayed index N is varied according to the movement of at least one of the first flange 14a and the second flange 14b.

The type of the index N is not particularly limited, and may be a numerical value indicating the size of a hand (glove size). When the index N is the glove size, the operator can grasp at a glance which glove size corresponds to at least one of the positions of the first flange 14a and the second flange 14b. As a result, the arrangement of the first flange 14a and the second flange 14b suitable for the operator can be attained at the time of injecting the intraocular lens 4, and the operation for injecting the intraocular lens 4 can be performed very smoothly.

The technical scope of the present invention is not limited to the embodiment described above but includes modes to which various modifications or improvements are made to the extent of deriving the specific effects obtained by the constituent features of the invention and combinations thereof.

For example, the intraocular lens injector of this embodiment may be, for example, a disposable type made of resin, or it may be a repeatedly usable type. However, the disposable type is preferable because it does not need to be cleaned and disinfected each time, which saves time and effort.

(Flange Movable in Axial Direction)

In this embodiment, a configuration with at least one of the first flange 14a and the second flange 14b having a configuration movable in the axial direction of the hollow body 5 has been described as a preferable example.

On the other hand, a vertically symmetrical flange 140 provided on the hollow body 50 of the conventional intraocular lens injector 1000, which is made movable in the axial direction of the hollow body 50, may be used in this embodiment.

In such a case, the distance between the tip end 5a of the hollow body 5 and the first flange 14a can be varied, tailored to the operator. This configuration can also be used to solve the problem to provide an intraocular lens injector 1 capable of smoothly performing an operation at the time of injecting an intraocular lens 4. Therefore, this configuration can be an invention by itself. Such a configuration is as follows.

An intraocular lens injector 1, including:
a hollow body 5 having a lens setting portion 11 on which an intraocular lens 4 is set;
plunger 9 that moves through an inside of the hollow body 5 in an axial direction of the hollow body 5;
pushing member 10 that pushes out the intraocular lens 4 from the lens setting portion 11 by moving together with the plunger 9, through the inside of the hollow body, and in the axial direction of the hollow body 5; and
flange 14 that is provided in the hollow body 5 and can move in an axial direction of the hollow body 5.

FIG. 9(a) is a schematic perspective view illustrating that the index N is configured to be varied according to the arrangement of the flange 14, before movement of the flange 14. FIG. 9(b) is a diagram after movement of the flange 14.

Figure 9:
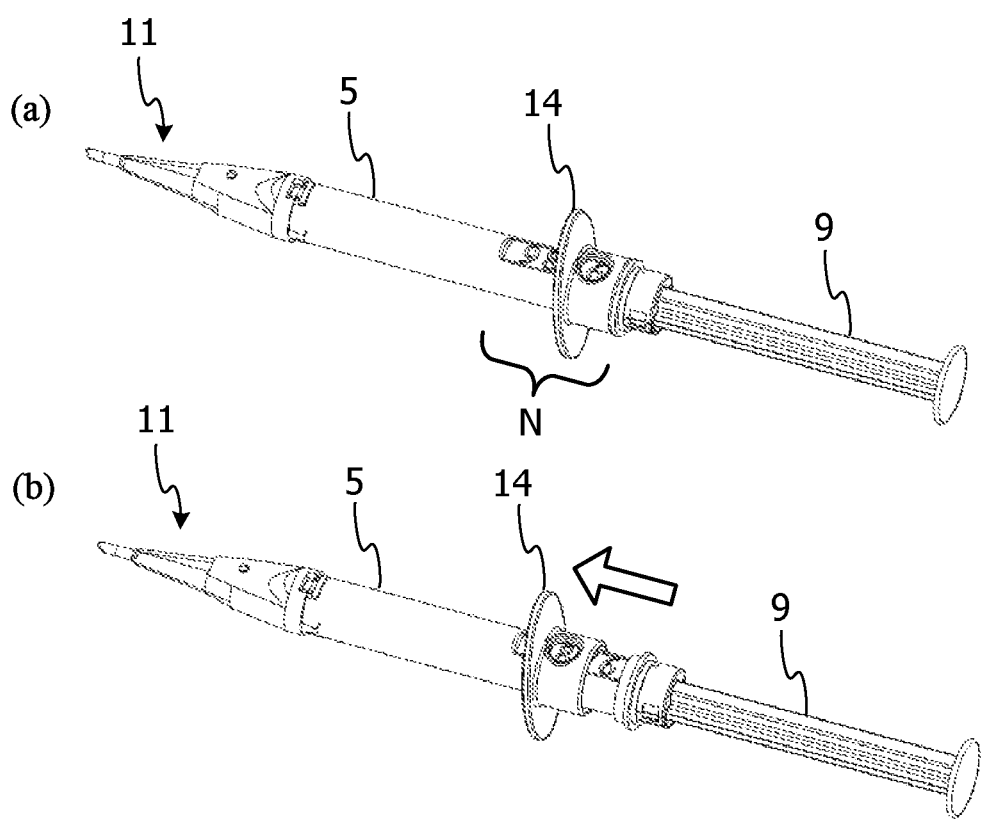
FIG. 9 is a schematic perspective view of a configuration in which a displayed index is varied according to the movement of the flange 14.

As illustrated in FIG. 9, when the index N is the glove size, the operator can grasp at a glance which glove size corresponds to the positions of the flange 14. As a result, the arrangement of the flange 14 suitable for the operator can be attained at the time of injecting the intraocular lens 4, and the operation for injecting the intraocular lens 4 can be performed very smoothly.

The flange 14 in the above-described configuration may be the only flange 14 in the intraocular lens injector 1. That is, it may be the only flange 14 before and after the movement of the flange 14. Alternatively, like the conventional flange 14, the flange 14 may be protruded from the outer circumference of the hollow body 5 so that the intraocular lens injector 1 is vertically symmetrical when viewed from the lateral direction.

(First Flange 14a Diverted as Adaptor)

The first flange 14a may be produced by integrally molding with the hollow body 5, or may be prepared as an adaptor 17 separated from the hollow body 5. For example, the adaptor 17 may be fixed to flange 140 of the conventional intraocular lens injector 1000, the flange 140 protruding in an annular shape when viewed from the axial direction of the hollow body 50.

Figure 10:
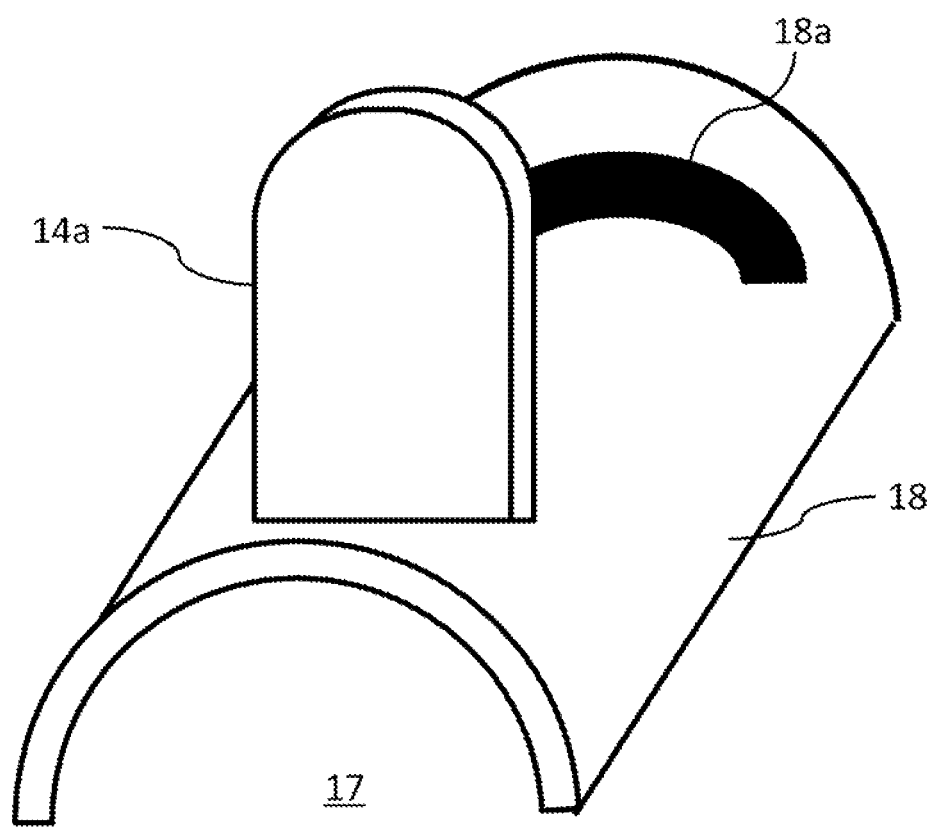
FIG. 10 is a schematic perspective view of an adaptor of the intraocular lens injector of this embodiment.

FIG. 10 is a schematic perspective view illustrating an adaptor 17 for an intraocular lens injector 1 of this embodiment.

By adopting this configuration, the effect of this embodiment can be enjoyed by engaging the adaptor 17 with the conventional intraocular lens injector 1000.

There is no particular limitation on this adaptor 17 as long as it is provided with the first flange 14a. Such a configuration is as follows.

An adaptor 17 for intraocular lens injector 1, including:
a hollow body 5 having a lens setting portion 11 on which an intraocular lens 4 is set;
plunger 9 that moves through an inside of the hollow body 5 in an axial direction of the hollow body 5;
pushing member 10 that pushes out the intraocular lens 4 from the lens setting portion 11 by moving together with the plunger 9, through the inside of the hollow body, and in the axial direction of the hollow body 5; and
second flange 14b protruded from an outer circumferential surface of the hollow body 5 (or the conventional flange 140);

wherein the adaptor 17 includes first flange 14a, when viewing the hollow body 5 from the axial direction after the adaptor 17 is attached to the intraocular lens injector 1, the hollow body is configured so that a shape of the first flange 14a on the A direction side toward a center of gravity G of the hollow body 5 in which the first flange 14a is arranged from a center O of the hollow body 5, and a shape of the first flange 14a on the A' direction side which is the opposite direction to the A direction, are non-symmetrical, and the second flange 14b is configured to protrude toward at least the A' direction, and the first flange 14a is configured not to protrude toward the A' direction, or configured so that a protruding distance Ha' of the first flange 14a toward the A' direction is smaller than a protruding distance Ha of the first flange 14a toward the A direction and smaller than a protruding distance Hb of the second flange 14b toward the A' direction.

Specific configurations of the adaptor 17 are as follows. For example, an adaptor body 18 is prepared having a semi-cylindrical shape which is a shape following the outer circumference of the hollow body 5. The first flange 14a is formed which is protruded from a semi-cylindrical outer circumferential surface of the adaptor body 18. A portion of the adaptor body 18, which is to be the rear end of the adaptor 17 when it is attached to the hollow body 5, is then provided with a configuration that can engage with the flange 140 of the conventional intraocular lens injector 1000.

There is no limitation on such an engageable aspect. For example, an opening 18a is provided in the adaptor body 18 behind the first flange 14a, and the adaptor 17 is fixed by putting the conventional flange 140 through the opening 18a upwardly from below. In that case, since the opening 18a can fix the conventional flange 140, the shape of the adaptor body 18 is not necessarily semi-cylindrical.

On the other hand, instead of or in addition to the flange 140 of the conventional intraocular lens injector 1000, the adaptor body 18 may be engaged with the outer circumference of the hollow body 5.

Another engageable aspect is to provide a distinct clip-shaped protrusion on the adaptor body 18 that is separated from the first flange 14a, the distinct protrusion locking the conventional flange 140 like a clip.

In order to reflect a suitable example of the separation distance L between the first flange 14a and the second flange 14b in this embodiment, the separation distance L between the opening 18a in the adaptor body 18 and the first flange 14a is preferably from 10 to 60 mm (more suitably from 10 to 35 mm). In the case of an aspect other than the opening 18a, when the adaptor 17 is attached to the intraocular lens injector 1, the adaptor 17 preferably has a configuration in which the separation distance L between the first flange 14a and the second flange 14b is 10 to 35 mm. Incidentally, the protruding distance Ha is preferably 10 to 20 mm, as in this embodiment.

Further, a configuration with at least one of the first flange 14a and the second flange 14b movable in the axial direction of the hollow body 5, as described in this embodiment, may be adopted for the above-described adaptor 17.

(First Flange 14a and Second Flange 14b Diverted as Adaptor)

The first flange 14a and the second flange 14b may be integrated, and then prepared as an adaptor 17 which is a distinct body separated from the hollow body 5. Such a configuration is as follows.

An adaptor 17 for intraocular lens injector 1, including:
a hollow body 5 having a lens setting portion 11 on which an intraocular lens 4 is set;
plunger 9 that moves through an inside of the hollow body 5 in an axial direction of the hollow body 5;
pushing member 10 that pushes out the intraocular lens 4 from the lens setting portion 11 by moving together with the plunger 9, through the inside of the hollow body, and in the axial direction of the hollow body 5;
wherein the adaptor 17 includes a first flange 14a and a second flange 14b,
when viewing the hollow body 5 from the axial direction after the adaptor 17 is attached to the intraocular lens injector 1,
the hollow body is configured so that a shape of the first flange 14a on the A direction side toward a center of gravity G of the hollow body 5 in which the first flange 14a is arranged from a center O of the hollow body 5, and a shape of the first flange 14a on the A' direction side which is the opposite direction to the A direction, are non-symmetrical, and
the second flange 14b is configured to protrude toward at least the A' direction, and
the first flange 14a is configured not to protrude toward the A' direction, or configured so that a protruding distance Ha' of the first flange 14a toward the A' direction is smaller than a protruding distance Ha of the first flange 14a toward the A direction and smaller than a protruding distance Hb of the second flange 14b toward the A' direction.

In this case, in addition to the first flange 14a, the second flange 14b is formed so as to be arranged on a rear end side with respect to the first flange 14a and protruded from the outer circumferential surface of the adaptor 18. In that case, the second flange 14b is made to protrude in a direction (A' direction) opposite to the protruding direction (A direction) of the first flange 14a. In this connection, the adaptor body 18 preferably is elastic and has an approximately C-shape, that is, a part of the cylinder being cut out in the longitudinal direction. With this shape, the hollow body 5 can be fit into the adaptor body 18 to fix the adaptor 17.

When this adaptor 17 is attached to the hollow body 5, the substantially C-shaped opening 18a is oriented in the right-left direction (horizontal direction). As a result, the first flange 14a can protrude upward from the outer circumferential surface on the tip end side of the adaptor 17, and the second flange 14b can protrude downward from the outer circumferential surface of the rear end side with respect to the first flange 14a.

DESCRIPTION OF SIGNS AND NUMERALS

1 Intraocular lens injector
4 Intraocular lens
5 Hollow body
5a Tip end (of hollow body)
9 Plunger
9' Rear end (of plunger)
10 Pushing member
11 Lens setting portion
11a Lid (of lens setting portion)

14a First flange
14b Second flange
14 Flange
17 Adaptor for intraocular lens injector
18 Adaptor body
18a Opening
110b Stopper

The invention claimed is:

1. An intraocular lens injector, comprising:
a hollow body having a lens setting portion on which an intraocular lens is set such that when an optical surface of the intraocular lens faces upwardly the optical surface faces in an A direction;
a plunger that moves through an inside of the hollow body in an axial direction of the hollow body;
a pushing member that pushes out the intraocular lens from the lens setting portion by moving together with the plunger, through the inside of the hollow body, and toward front part of the axial direction of the hollow body;
a first flange, integrally formed with the hollow body, that protrudes in the A direction from an outer circumferential surface of the hollow body when viewed in the axial direction and is configured to receive a finger on a tip end side thereof; and
a second flange arranged on a rear end side with respect to the first flange and that protrudes in an A' direction, which is opposite the A direction, from the outer circumferential surface of the hollow body when viewed in the axial direction and is configured to receive a finger on a tip end side thereof,
wherein the hollow body is configured so that a shape on the A direction side toward a center of gravity of the hollow body in which the first flange is arranged from a center of the hollow body and a shape on the A' direction side are non-symmetrical when viewed from the axial direction, and
the first flange is configured not to protrude toward the A' direction, or configured so that a protruding distance of the first flange toward the A' direction is smaller than a protruding distance of the first flange toward the A direction and smaller than a protruding distance of the second flange toward the A' direction.

2. The intraocular lens injector according to claim 1, wherein the first flange and the second flange protrude 10 mm or more.

3. The intraocular lens injector according to claim 1, wherein the lens setting portion is arranged on a tip end side with respect to the first flange, and the lens setting portion is arranged in the A direction when viewing the hollow body from the axial direction.

4. The intraocular lens injector according to claim 1,
wherein the first flange and the second flange protrude 10 mm or more,
the lens setting portion is arranged on a tip end side with respect to the first flange, and
the lens setting portion is arranged in the A direction, when viewing the hollow body from the axial direction.

5. The intraocular lens injector according to claim 1, wherein at least one of the first flange and the second flange has a configuration movable in the axial direction of the hollow body.

6. The intraocular lens injector according to claim 5, wherein indexes corresponding to at least one of the first flange and the second flange are provided to the hollow body, and at least one of the displayed indexes is varied according to a movement of at least one of the first flange and the second flange.

7. An intraocular lens injector, comprising:
a hollow body that defines an outer surface, a tip end, a rear end, an axial direction and a center;
a lens setting portion associated with the hollow body;
a plunger configured to move through the hollow body in the axial direction;
a pushing member operably connected to the plunger;
a first flange that protrudes in an A direction from the outer surface of the hollow body when viewed in the axial direction, that does not protrude in an A' direction which is the opposite of the A direction, that defines a tip end facing side that faces the tip end of the hollow body, that is movable in the axial direction, and that is configured to receive an index finger of a hand on a tip end facing side while a thumb of the hand is on the plunger; and
a second flange that is located rearward of the first flange, that protrudes from the outer surface in the A direction and in the A' direction when viewed in the axial direction, that defines a tip end facing side that faces the tip end of the hollow body, that is movable in the axial direction, and that is configured to receive a middle finger of the hand on a tip end facing side while the thumb of the hand is on the plunger;
wherein a center of gravity is defined by the hollow body and the first flange and the A direction is a direction that extends upwardly from the center of the hollow body through the center of gravity.

8. The intraocular lens injector according to claim 7, wherein the first flange and the second flange protrude 10 mm or more.

9. The intraocular lens injector according to claim 7, wherein the lens setting portion faces the A direction.

10. The intraocular lens injector according to claim 7, wherein the hollow body includes indexes corresponding to at least one of the first flange and the second flange.

11. An intraocular lens injector, comprising:
a hollow body that defines an outer surface, a tip end, a rear end, an axial direction and a center;
a lens setting portion associated with the hollow body;
a plunger configured to move through the hollow body in the axial direction;
a pushing member operably connected to the plunger;
a first flange that protrudes in an A direction from the outer surface of the hollow body when viewed in the axial direction, that does not protrude in an A' direction which is the opposite of the A direction, that defines a tip end facing side that faces the tip end of the hollow body, and that is configured to receive an index finger of a hand on a tip end facing side while a thumb of the hand is on the plunger; and
a second flange that is located rearward of the first flange, that protrudes from the outer surface in the A direction and in the A' direction when viewed in the axial direction, that defines a tip end facing side that faces the tip end of the hollow body, and that is configured to receive a middle finger of the hand on a tip end facing side while the thumb of the hand is on the plunger;
wherein a center of gravity is defined by the hollow body and the first flange and the A direction is a direction that extends upwardly from the center of the hollow body through the center of gravity; and wherein the first flange is movable in the axial direction and the hollow body is configured to lock the first flange at different axial positions.

12. The intraocular lens injector according to claim 11, wherein the first flange and the second flange protrude 10 mm or more.

13. The intraocular lens injector according to claim 11, wherein the lens setting portion faces the A direction.

14. The intraocular lens injector according to claim 11, wherein the hollow body includes indexes corresponding to the first flange.

* * * * *